United States Patent [19]

Strauch et al.

[11] Patent Number: 5,637,489

[45] Date of Patent: Jun. 10, 1997

[54] PHOSPHINOTHRICIN-RESISTANCE GENE, AND ITS USE

[75] Inventors: Eckhard Strauch; Wolfgang Wohlleben; Walter Arnold; Renate Alijah; Alfred Pühler, all of Bielefeld; Gerhard Wöhner, Flörsheim am Main; Rüdiger Marquardt, Frankfurt am Main; Susanne Grabley, Königstein/Taunus; Dieter Brauer, Flörsheim am Main; Klaus Bartsch, Kelkheim, all of Germany

[73] Assignee: Hoechst Aktiengesellschaft, Frankfurt am Main, Germany

[21] Appl. No.: 487,695

[22] Filed: Jun. 7, 1995

Related U.S. Application Data

[60] Continuation of Ser. No. 115,651, Sep. 3, 1993, abandoned, which is a division of Ser. No. 795,275, Nov. 20, 1991, Pat. No. 5,273,894, which is a continuation of Ser. No. 605,131, Oct. 31, 1990, which is a continuation of Ser. No. 88,118, Aug. 21, 1987.

[30] Foreign Application Priority Data

| Aug. 23, 1986 | [DE] | Germany | 36 28 747.4 |
| Nov. 3, 1986 | [DE] | Germany | 36 37 307.9 |
| Dec. 16, 1986 | [DE] | Germany | 36 42 829.9 |
| Jan. 8, 1987 | [DE] | Germany | 37 00 313.5 |

[51] Int. Cl.$^6$ ............................ C12N 15/05; C12N 15/00
[52] U.S. Cl. .......................................................... 435/172.3
[58] Field of Search ............................ 435/69.1, 91.1, 435/172.1, 172.3, 193, 320.1, 252.3–252.35, 128, 129, 240.1, 240.4; 800/205; 935/14, 67, 72, 75; 536/23.2, 23.7

[56] References Cited

U.S. PATENT DOCUMENTS 5,273,894  12/1993  Strauch et al. ........................... 435/129

FOREIGN PATENT DOCUMENTS

| 0 159 418 | 10/1985 | European Pat. Off. . |
| 0173327 | 3/1986 | European Pat. Off. . |
| 0 242 246 | 10/1987 | European Pat. Off. . |
| 86/02097 | 4/1986 | WIPO . |
| 87/05629 | 9/1987 | WIPO . |

OTHER PUBLICATIONS

Vaeck et al., UCLA Symposium on Molecular and Cellular Biology New Series, vol. 62, Plant Gene Systems and Their Biology, pp. 171–181, Alan R. Liss, Inc., (1987).

Wohlleben et al., Gene 70:25–37 (1988).

Shah et al., Science 233:478–481 (Jul. 25, 1986).

Dodds, Plant Genetic Engineering, Cambridge University Press, Cambridge, pp. 1–3, 1985.

Jones, In Dodds, Plant Genetic Engineering, Cambridge University Press, Cambridge, pp. 269–295, 1985.

Gasser et al., Science 244:1293–1299 (1989).

*Primary Examiner*—James Martinell
*Attorney, Agent, or Firm*—Finnegan, Henderson, Farabow, Garrett & Dunner, L.L.P.

[57] ABSTRACT

Selection of *Streptomyces viridochromogenes* DSM 4112 for resistance to phosphinothricyl-alanyl-alanine (PTT) results in PTT-resistance selectants. The DNA fragment which carries the phosphinothricin(PTC)-resistance gene is obtained from the total DNA of these selectants by cutting with BamHI, cloning of a fragment 4.0 kb in size, and selection for PTT resistance. This gene is suitable for the production of PTC-resistant plants, and as a resistance marker and for the selective N-acetylation of the L-form of racemic PTC.

6 Claims, 1 Drawing Sheet

PHOSPHINOTHRICIN-RESISTANCE GENE, AND ITS USE

This application is a continuation of application Ser. No. 08/115,651, filed Sep. 3, 1993, now abandoned, which is a division application of Ser. No. 07/795,275 filed Nov. 20, 1991, now U.S. Pat. No. 5,273,894 which is a continuation application of Ser. No. 07/605,131 filed Oct. 31, 1990, which is a continuation application of Ser. No. 07/088,118 filed Aug. 21, 1987.

Phosphinothricin (PTC, 2-amino-4-methylphosphinobutyric acid) is an inhibitor of glutamine synthetase. PTC is a "structural unit" of the antibiotic phosphinothricyl-alanyl-alanine. This tripeptide (PTT) is active against Gram-positive and Gram-negative bacteria as well as against the fungus Botrytis cinerea (Bayer et al., Helv. Chim. Acta 55 (1972) 224). PTT is produced by the strain Streptomyces viridochromogenes Tü 494 (DSM 40736, DSM 4112).

German Patent 2,717,440 discloses that PTC acts as a total herbicide. The published PCT Application WO 86/02097 describes plants whose resistance to PTC is attributable to overproduction of glutamine synthetase. Overproduction of this type, for example resulting from gene amplification, entails the risks of instability. Hence, such an instability would be associated with a decrease in the overproduction of glutamine synthetase, and the competitive inhibitory action of PTC would reappear.

In contrast, the invention, which is defined in the patent claims, relates to a PTC-resistance gene and to its use for the production of PTC-resistant plants. In addition, this gene can also be used as a resistance marker. Furthermore, the gene is suitable for the selective N-acetylation of the L-form of racemic PTC.

Figure 1:
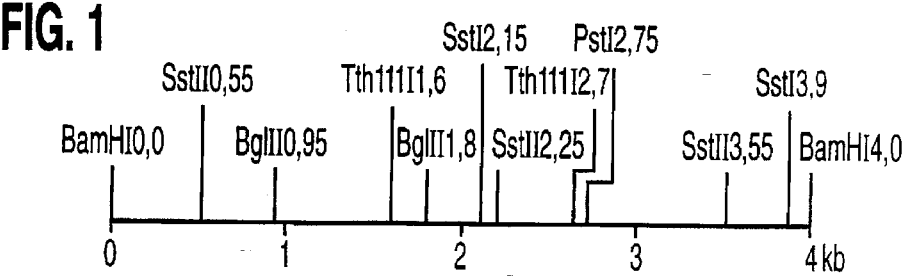
FIG. 1 is a restriction map of a 4.0 Kb fragment of DNA from S. viridochromogenes DSM 4112.

The PTC-resistance gene according to the invention can be obtained by cutting, with BamHI, the total DNA from Streptomyces viridochromogenes DSM 4112 which has been selected for PTT resistance, by cloning a fragment 4.0 kb in size, and by selection for PTT resistance. The restriction map (FIG. 1) details the characteristics of this 4.0 kb fragment.

Cloning experiments on sections of this 4 kb fragment were carried out to localize the position of the coding region more accurately. It emerged from this that the resistance gene is located on the 1.6 kb SstII-SstI fragment (positions 0.55 to 2.15 in FIG. 1). Digestion with BglII resulted in the fragment which is 0.8 kb in size and which, after incorporation into a plasmid and transformation of S. lividans, confers PTT resistance. This resistance is caused by N=acetylation of PTC.

Maxam and Gilbert sequencing of the 0.8 kb fragment reveals DNA sequence I (Annex). The position of the resistance gene can be determined from the open reading frame of this sequence (from position 258). the end of the gene is located at the penultimate nucleotide shown (position 806), i.e. the last nucleotide (position 807) is the first of the stop codon.

The Shine-Dalgarno sequence in DNA sequence I is emphasized by underlining, as is the GTG acting as start codon. Thus, the top line depicts the definitive reading frame.

DNA sequence II shows the restriction sites within the sequenced gene. Enzymes which cut the sequence more than six times are not indicated.

The antibiotic PTT is taken up by bacteria and broken down to PTC. The latter also inhibits glutamine synthetase in bacteria, so that the bacteria die of a lack of glutamine. Hence, PTT-producing bacteria ought to have a mechanism which protects them from the action of PTT, that is to say either prevents reuptake of the PTT which has been produced or permits a modification of the breakdown product PTC. However, surprisingly, the PTT producer S. viridochromogenes DSM 4112 is sensitive to its own antibiotic. Unexpectedly, it proved possible, however, by selection for PTT resistance to find, at the surprisingly high rate of $10^{-5}$, selectants which are resistant to PTT and, moreover, suppress the background growth of adjacent colonies.

A gene bank was set up from the DNA of these selectants by isolating the DNA and cleaving it with BamHI and ligating it into a Streptomycetes vector. The ligation mixture was transformed into the commercially available strain S. lividans TK 23, resulting in about 5000 to 10000 transformants having an insert of about 1 to 5 kb per 1 μg of ligation mixture. Among the transformants there were PTT-resistant S. lividans strains. It was possible, by isolation of the plasmids and retransformation into S. lividans, to show that the resistance is plasmid-coded. The gene responsible for the resistance is located on a 4 kb BamHI fragment (FIG. 1). The coding region is located on the 0.8 kb BglII fragment. The BamHI fragment contains no cleavage sites for the enzymes ClaI, EcoRI, EcoRV, HindIII, HpaI, KpnI, PvuI, PvuII and XhoI.

Comparison with the restriction map of a resistance gene, which has not been characterized in detail, for S. hygroscopicus FERM BP-130/ATCC 21705 (European Patent Application with the publication no. 0,173,327, FIG. 7) shows that the resistance gene according to the invention differs from the known gene, which was found during the search for PTT biosynthesis genes.

It was possible to show, by incubation of cell extracts from S. viridochromogenes DSM 4112 and S. lividans TK 23 on the one hand, and the PTT-resistant S. viridochromogenes selectants and a plasmid-carrying S. lividans transformant, on the other hand, with PTC and acetyl-coenzyme A that the latter cells have acetylating activity.

Chromatography tests show that the acetylation takes place on the amino group.

Since PTT-resistance has also been found in E. coli, and thus the resistance mechanism also functions in Gram-negative bacteria, it is possible to rule out resistance based on transport phenomena. Thus, after coupling to plant promoters and using suitable vectors, the resistance gene according to the invention can be transformed into plants, and in this way PTC-resistant plants can be produced.

The N-acetylation of PTC can also be used for racemate resolution of synthetic, D,L-PTC since selective acetylation of only the L-form takes place.

Thus the invention also relates to the use of the resistance gene for the selective N-acetylation of the L-form of racemic PTC.

The PTC acetyltransferase coded for the resistance gene according to the invention can thus be used to separate racemic PTC, as can be obtained, for example, by the method of German Patent 2,717,440, into the optical antipodes by exposing the racemate to the acetylating action of this enzyme, since there is selective attach on the L-form while the D-form remains unchanged. The mixture thus obtained can then be fractionated in a manner known per se on the basis of the differences in properties.

The contacting of N-acyl-D,L-amino acids with acylases, which are immobilised on carriers where appropriate, with selective liberation of the L-amino acid, which can be extracted with water-immiscible solvents from the mixture with the N-acyl-D-amino acid after acidification, has been disclosed (British Patent 1,369,462). A corresponding fractionation of N-acyl-D,L-PTC is disclosed, for example, in German Offenlegungschrift 2,939,269 or U.S. Pat. No. 4,226,941.

The D-PTC which remains according to the invention can be racemized in known manner (European Patent Application with the publication no. (EP-A) 0,137,371, example 8), and then returned to the process.

It is possible, but not necessary, to isolate the enzyme, this also being intended to mean, here and hereinafter, always the enzymatically active part. If the enzyme is isolated, it can be used in the free form or the form immobilised on a carrier. Examples of suitable carriers are described in EP-A 0,141, 223. However, it is expedient not to isolate the enzyme but to use any desired PTC-resistant cells which express the enzyme according to the invention. Thus, it is possible and expedient to use the PTT-resistant selectants of S. viridochromogenes DSM 4112. Moreover, it is possible and advantageous to use any desired cell which has been transformed with the gene according to the invention and which is able to express PTC acetyltransferase. In this connection, the gene according to the invention, this also being intended to mean active parts thereof, can be introduced into the host cell in plasmid-integrated form or by using other customary methods of gene manipulation, for example by transfection. For example, incorporation into a E. coli expression plasmid and transformation of E. coli with such a plasmid is expedient, for example by the methods known from EP-A 0,163,249 and 0,171,024.

For the N-acetylation, according to the invention, of L-PTC in the racemate the cells which express PTC acetyltransferase can be used in the free or immobilised form, with the customary methods of immobilisation being used (for example German Offenlegungsschrift 3,237,341 and literature cited therein).

The enzymatic acetylation, according to the invention, of L-PTC is carried out in the manner customary for enzymatic reactions, with the conditions of the method being governed by the characteristics of the organism used. In principle, methods suitable for this are the same as for the abovementioned selective deacylation method.

The invention is illustrated in detail in the examples which follow. Unless otherwise stated, parts and percentage data relate to weight.

EXAMPLE 1

PTT-Resistant Selectants

The strain S. viridochromogenes DSM 4112 was cultured on minimal medium (Hopwood et al., Genetic Manipulation of Streptomyces, A Laboratory Manual, The John Innes Foundation, Norwich, England (1985), page 233) and increasing concentrations of PTT were added. At a concentration of 100 µg/ml one resistant colony was found per $10^5$ colonies, approximately.

EXAMPLE 2

Preparation of the Vector

Figure 2:
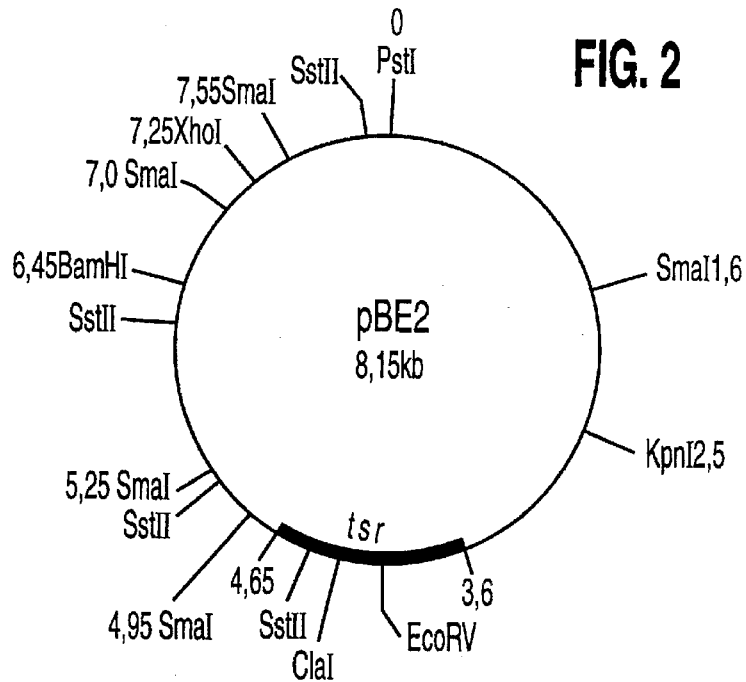
FIG. 2 is a restriction may of pEB2.

The plasmid pSVH1 (European Patent 0,070,522; U.S. Pat. No. 4,673,642) is cut with BglII, and the fragment about 7.1 kb in size is isolated and ligated with the 1.1 kb BclI fragment having thio-strepton resistance (European Patent Application with the publication number 0,158,201). The plasmid pEB2 which is about 8.15 kb in size is obtained (FIG. 2).

EXAMPLE 3

Isolation of the Resistance Gene

Figure 3:
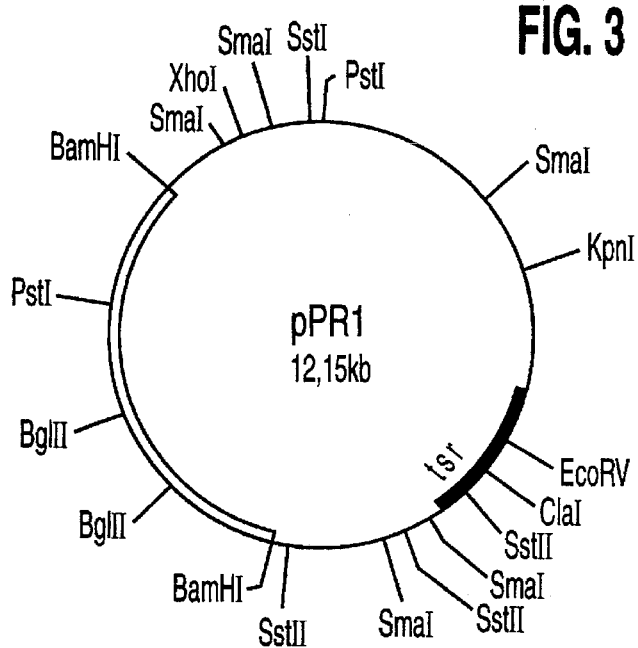
FIG. 3 is a restriction map of pPR1.

The total DNA is isolated from the selectants obtained in example 1, and it is cleaved with BamHI. The plasmid pEB2 is likewise opened with BamHI, and the two mixtures are combined and ligated. The ligation mixture is transformed into S. lividans TK 23 (obtainable from the John Innes Foundation), with 5000 to 10000 transformants having an insert of about 1–5 kb being obtained per 1 µg of ligation mixture. Selection for PTT-resistance produces two resistant S. lividans colonies. The plasmid which as been taken up is isolated from the latter and is cut with BamHI. A 4 kb BamHI fragment which carries the gene responsible for resistance is found. This plasmid was celled pPR1 (FIG. 3).

Retransformation into S. lividans TK 23 shows, that the PTT-resistance is plasmid-coded, since the transformants grow on minimal medium containing 100 µg/ml PTT.

EXAMPLE 4

Demonstration of the Inactivation of PTC by N-acetylation

The following strains were examined to demonstrate the acetylating activity of the cloned fragment: S. viridochromogenes DSM 40736, S. viridochromogenes (PTT-resistant mutant), S. lividans TK23 and S. lividans TK 23 (pPR1).

This entails the strains being inoculated into lysis medium A (European Patent Application with the publication number 0,158,872, page 6) and incubated at 30° C. in an orbital shaker for 2 days. After harvesting, 1 mg of mycelium is disrupted with ultrasound in a suitable buffer (for example RS buffer: C. J. Thompson et al., J. Bacteriol. 151 (1982), 678–685). The procedure for a typical experiment to measure PTC breakdown is as follows:

100 µl of PTC solution (250 µg/ml) and 50 µl of acetyl-CoA (4 mg/ml) are added to 250 µl of crude extract, and the mixture is incubated at 30° C. for 2 hours. The amounts of PTC which are still present after this time are measured by HPLC. The results of this are as follows:

| Strain | unreacted PTC / introduced PTC |
| --- | --- |
| S. lividans TK23 | 100% |
| S. viridochromogenes (DSM 40736) | 72% |
| S. viridochromogenes Selectant | 7% |
| S. lividans TK23 (pPR1) | 31% |

A comparison with reference substances on thin-layer chromatography (no stain with ninhydrin) demonstrates that N-acetylation of the PTC has taken place.

DNA Sequence I

IleTrpSerAspValLeuGlyAlaGlyProValLeuProGlyAspAspPhePheSerLeuGlyGlyThrSerIle

AspLeuGluArgArgProGlyGlyArgSerGlyAlaAlaArgGlyArgLeuLeuLeuProArgArgHisLeuHis

ArgSerGlyAlaThrSerTrpGlyProValArgCysCysProGlyThrThrSerSerProSerAlaAlaProPro

AGATCVTGGAGCGACGTCCTGGGGGCCGGTCCGGTGCTGCCCGGGGACGACTTCTTCTCCCTCGGCGGCACCTCCA 75

TCTAGACCTCGCTGCAGGACCCCCGGCCAGGCCACGACGGGCCCCTGCTGAAGAAGAGGGAGCCGCCGTGGAGGT

SerArgSerArgArgGlyProProArgAspPeoAlaAlaArgProArgSerArgArgGlyArgArgCysArgTrp

AspProAlaValAspGlnProGlyThrArgHisGlnGlyProValValGluGluGlyGluAlaAlaGlyGlyAsp

IleGlnLeuSerThrArgProAlaProGlyThrSerGlyProSerSerLysLysGluArgProProValGluMet

SerAlaLeuArgValValSerArgIleArgLysGluLeuGlyValProLeuArgLeuAlaValIlePheGluThr

LeuGlyValAlaGlyGlyLeuAlaHisProGlnGlyThrArgArgAlaThrProAlaArgArgAspLeuArgAsp

SerArgArgCysGlyTrpSerArgAlaSerAlaArgAsnSerAlaCysHisSerGlySerProOP SerSerArg

TCTCGGCGTTGCGGGTGGTCTCGCGCATCCGCAAGGAACTCGGCGTGCCACTCCGGCTCGCCGTGATCTTCGAGA 150

AGAGCCGCAACGCCCACCAGAGCGCGTAGGCGTTCCTTGAGCCGCACGGTGAGGCCGAGCGGCACTAGAAGCTCT

ArgProThrAlaProProArgAlaCysGlyCysProValArgArgAlaValGlyAlaArgArgSerArgArgSer

ArgArgGlnProHisAspArgAlaAspAlaLeuPheGluAlaHisTrpGluProGlyHisAspGluLeuArg

GluAlaAsnArgThrThrGluArgMetArgLeuSerSerProThrGlySerArgSerAlaThrIleLysSerVal

ProSerLeuGluAlaValAlaGluSerValLeuArgGluLeuLysGlyThrAM OC ArgGlyAlaArgHisPro

AlaValProGlySerGlyGlyArgIleArgThrProArgThrGluGlyAspValValLysArgCysProProPro

ArgArgProTrpLysArgTrpProAsnProTyrSerAlaAsnOP ArgGlyArgSerArgSerLysGluValProAlaThr

CGCCGTCCCTGGAAGCGGTGGCCGAATCCGTACTCCGCGAACTGAAGGGGACGTAGTAAAGAGGTGCCCGCCACC 225

GCGGCAGGGACCTTCGCCACCGGCTTAGGCATGAGGCGCTTGACTTCCCCTGCATCATTTCTCCACGGGCGGTGG

AlaThrGlyProLeuProProArgIleArgValGlyArgValSerProSerThrThrPheLeuHisGlyGlyGly

ArgGlyGlnPheArgHisGlyPheGlyTyrGluAlaPheGlnLeuProArgLeuLeuSerThrGlyAlaValArg

GlyAspArgSerAlaThrAlaSerAspThrSerArgSerSerPheProValTyrTyrLeuProAlaArgTrpGly

LeuSerGlnAsnThrGluGlyArgProHisValSerProGluArgArgProValGluIleArgProAlaThrAla

AlaPheAlaGluHisArgArgLysThrThrArgGluProArgThrThrProGlyArgAspProSerArgHisArg

ArgPheArgArgThrProLysGluAspHisThrOP AlaGlnAsnAspAlaArgSerArgSerValProProPro

CGCTTTCGCAGAACACCGA<u>AGGAAG</u>ACCACAC<u>GTG</u>AGCCCAGAACGACGCCCGGTCGAGATCCGTCCCGCCACCG 300

GCGAAAGCGTCTTGTGGCTTCCTTCTGGTGTGCACTCGGGTCTTGCTGCGGGCCAGCTCTAGGCAGGGCGGTGGC

AlaLysAlaSerCysArgLeuPheValValArgSerGlyLeuValValGlyProArgSerGlyAspArgTrpArg

LysArgLeuValGlyPheSerSerTrpValHisAlaTrpPheSerAlaArgAspLeuAspThrGlyGlyGlyGly

SerGluCysPheValSerProLeuGlyCysThrLeuGlySerArgArgGlyThrSerIleArgGlyAlaValAla

AlaAspMetAlaAlaValCysAspIleValAsnHisTyrIleGluThrSerThrValAsnPheArgThrGluPro

ArgArgHisGlyGlyGlyLeuArgHisArgGlnSerLeuHisArgAspGluHisGlyGlnLeuProTyrGlyAla

ProProThrTrpArgArgSerAlaThrSerSerIleThrThrSerArgArgAlaArgSerThrSerValArgSer

GCGCCGACATGGCGGCGGTCTGCGACATCGTCAATCACTACATCGAGACGAGCACGGTCAACTTCCGTACGGAGC 375

GGCGGCTGTACCGCCGCCAGACGCTGTAGCAGTTAGTGATGTAGCTCTGCTCGTGCCAGTTGAAGGCATGCCTCG

ArgArgCysProProProArgArgCysArgOP AspSerCysArgSerSerCysProOP SerGlyTyrProAla

GlyValHisArgArgAspAlaValAspAspIleValValAspLeuArgAlaArgAspValGluThrArgLeuArg

-continued

AlaSerMetAlaAlaThrGlnSerMetThrLeuOP AM MetSerValLeuValThrLeuLysArgValSerGly

GlnThrProGlnGluTrpIleAspAspLeuGluArgLeuGlnAspArgTyrProTrpLeuValAlaGluValGlu

AlaAspSerAlaGlyValAspArgArgProGlyAlaProProGlyProLeuProLeuAlaArgArgArgGlyGly

ArgArgLeuArgArgSerGlySerThrThrTrpSerAlaSerArgThrAlaThrProGlySerSerProArgTrp

CGCAGACTCCGCAGGAGTGGATCGACGACCTGGAGCGCCTCCAGGACCGCTACCCCTGGCTCGTCGCCGAGGTGG 450

GCGTCTGAGGCGTCCTCACCTAGCTGCTGGACCTCGCGGAGGTCCTGGCGATGGGGACCGAGCAGCGGCTCCACC

AlaSerGluAlaProThrSerArgArgGlyProAlaGlyGlyProGlySerGlyArgAlaArgArgArgProPro

LeuSerArgLeuLeuProAspValValGlnLeuAlaGluLeuValAlaValGlyProGluAspGlyLeuHisLeu

CysValGlyCysSerHisIleSerSerArgSerArgArgTrpSerArgAM GlyGlnSerThrAlaSerThrSer

GlyValValAlaGlyIleAlaTyrAlaGlyProTrpLysAlaArgAsnAlaTyrAspTrpThrValGluSerThr

GlyArgArgArgArgHisArgLeuArgArgProLeuGluGlyProGlnArgLeuArgLeuAspArgArgValAsp

ArgAlaSerSerProAlaSerProThrProAlaProGlyArgProAlaThrProThrThrGlyProSerSerArg

AGGGCGTCGTCGCCGGCATCGCCTACGCCGGCCCCTGGAAGGCCCGCAACGCCTACGACTGGACCGTCGAGTCGA 525

TCCCGCAGCAGCGGCCGTAGCGGATGCGGCCGGGGACCTTCCGGGCGTTGCGGATGCTGACCTGGCAGCTCAGCT

ProArgArgArgArgCysArgArgArgArgGlyArgSerProGlyCysArgArgArgSerSerArgArgThrSer

AlaAspAspGlyAlaAspGlyValGlyAlaGlyProLeuGlyAlaValGlyValValProGlyAspLeuArgArg

ProThrThrAlaProMetAlaAM AlaProGlyGlnPheAlaArgLeuAlaAM SerGlnValThrSerAspVal

ValTyrValSerHisArgHisGlnArgLeuGlyLeuGlySerThrLeuTyrThrHisLeuLeuLysSerMetGlu

GlyValArgLeuProProAlaProAlaAlaArgThrGlyLeuHisProLeuHisProProAlaGluValHisGly

ArgCysThrSerProThrGlyThrSerGlySerAspTrpAlaProProSerThrProThrCysOP SerProTrp

CGGTGTACGTCTCCCACCGGCACCAGCGGCTCGGACTGGGCTCCACCCTCTACACCCACCTGCTGAAGTCCATGG 600

GCCACATGCAGAGGGTGGCCGTGGTCGCCGAGCCTGACCCGAGGTGGGAGATGTGGGTGGACGACTTCAGGTACC

ProThrArgArgGlyGlyAlaGlyAlaAlaArgValProSerTrpGlyArgCysGlyGlyAlaSerThrTrpPro

HisValAspGlyValProValLeuProGluSerGlnAlaGlyGlyGluValGlyValGlnGlnLeuGlyHisLeu

ThrTyrThrGluTrpArgCysTrpArgSerProSerProGluValArgAM ValTrpArgSerPheAspMetSer

AlaGlnGlyPheLysSerValValAlaValIleGlyLeuProAsnAspProSerValArgLeuHisGluAlaLeu

GlyProGlyLeuGlnGluArgGlyArgArgHisArgThrAlaGlnArgProGluArgAlaProAlaArgGlyAla

ArgProArgAlaSerArgAlaTrpSerProSerSerAspCysProThrThrArgAlaCysAlaCysThrArgArg

AGGCCCAGGGCTTCAAGAGCGTGGTCGCCGTCATCGGACTGCCCAACGACCCGAGCGTGCGCCTGCACGAGGCGC 875

TCCGGGTCCCGAAGTTCTCGCACCAGCGGCAGTAGCCTGACGGGTTGCTGGGCTCGCACGCGGACGTGCTCCGCG

ProGlyProSerOP SerArgProArgArgOP ArgValAlaTrpArgGlySerArgAlaGlyAlaArgProAla

GlyLeuAlaGluLeuAlaHisAspGlyAspAspSerGlnGlyValValArgAlaHisAlaGlnValLeuArgGlu

AlaTrpProLysLeuLeuThrThrAlaThrMetProSerGlyLeuSerGlyLeuThrArgArgCysSerAlaSer

GlyTyrThrAlaArgGlyThrLeuArgAlaAlaGlyTyrLysHisGlyGlyTrpHisAspValGlyPheTrpGln

ArgIleHisArgAlaArgAspAlaAlaGlySerArgLeuGlnAlaArgGlyLeuAlaArgArgGlyValLeuAla

SerAspThrProArgAlaGlyArgCysGlyGlnProAlaThrSerThrGlyAlaGlyThrThrTrpGlySerGly

TCGGATACACCGCGCGCGGGACGCTGCGGGCAGCCGGCTACAAGCACGGGGGCTGGCACGACGTGGGGTTCTGGC 750

AGCCTATGTGGCGCGCGCCCTGCGACGCCCGTCGGCCGATGTTCGTGCCCCCGACCGTGCTGCACCCCAAGACCG

ArgIleCysArgAlaArgSerAlaAlaProLeuArgSerCysAlaArgProSerAlaArgArgProThrArgAla

SerValGlyArgAlaProArgGlnProCysGlyAlaValLeuValProAlaProValValHisProGluProLeu

ProTyrValAlaArgProValSerArgAlaAlaProAM LeuCysProProGlnCysSerThrProAsnGlnCys

ArgAspPheGluLeuProAlaProProArgProValArgProValThrGlnIle

AlaArgLeuArgAlaAlaGlyProAlaProProArgProAlaArgHisThrAsp

SerAlaThrSerSerCysArgProArgProAlaProSerGlyProSerHisArgSer

AGCGCGACTTCGAGCTGCCGGCCCCGCCCCGCCCCGTCCGGCCCGTCACACAGATCT 807

TCGCGCTGAAGCTCGACGGCCGGGGCGGGGCGGGGCAGGCCGGGCAGTGTGTCTAGA

AlaArgSerArgAlaAlaProGlyAlaGlyGlyArgGlyAlaArgOP ValSerArg

AlaValGluLeuGlnArgGlyArgGlyAlaGlyAspProGlyAspCysLeuAsp

ArgSerLysSerSerGlyAlaGlyGlyArgGlyThrArgGlyThrValCysIle

DNA Sequence II

1 AGATCTGGAGCGACGTCCTGGGGGCCGGTCCGGTGCTGCCCGGGGACGACTTCTTCTCCC

TCTAGACCTCGCTGCAGGACCCCCGGCCAGGCCACGACGGGCCCCTGCTGAAGAAGAGGG

1 BGLII XHOII, 2 DPNI SAU3A, 5 GSUI, 12 AATII ACYI, 13 MAEII

, 17 APYI ECORII, 26 RSRII, 27 AVAII, 35 BBVI, 39 AVAI NCII

SMAI, 40 NCII, 52 MBOII, 59 MNLI,

61 TCGGCGGCACCTCCATCTCGGCGTTGCGGGTGGTCTCGCGCATCCGCAAGGAACTCGGCG

AGCCGCCGTGGAGGTAGAGCCGCAACGCCCACCAGAGCGCGTAGGCGTTCCTTGAGCCGC

66 HGICI, 70 MNLI, 97 FNUDII, 100 SFANI62 , 101 FOKI,

121 TGCCACTCCGGCTCGCCGTGATCTTCGAGACGCCGTCCCTGGAAGCGGTGGCCGAATCCG

ACGGTGAGGCCGAGCGGCACTAGAAGCTCTGCGGCAGGGACCTTCGCCACCGGCTTAGGC

122 BGLI, 140 DPNI SAU3A, 142 MBOII, 149 ACYI HGAI TTH111I,

158 APYI ECORII, 169 CFRI GDIII, 174 HINFI, 180 RSAI,

181 TACTCCGCGAACTGAAGGGGACGTAGTAAAGAGGTGCCCGCCACCCGCTTTCGCAGAACA

ATGAGGCGCTTGACTTCCCCTGCATCATTTCTCCACGGGCGGTGGGCGAAAGCGTCTTGT

186 FNUDII, 201 MAEII, 211 MNLI, 213 HGICI, 214 SDUI,

241 CCGAAGGAAGACCACACGTGAGCCCAGAACGACGCCCGGTCGAGATCCGTCCCGCCACCG

GGCTTCCTTCTGGTGTGCACTCGGGTCTTGCTGCGGGCCAGCTCTAGGCAGGGCGGTGGC

247 MBOII, 254 AFLIII, 255 PMACI, 256 MAEII, 260 HGIJII SDUI

, 271 ACYI HGAI, 275 NCII, 283 XHOII, 284 BINI DPNI SAU3A,

301 CCGCCGACATGGCGGCGGTCTGCGACATCGTCAATCACTACATCGAGACGAGCACGGTCA

GGCGGCTGTACCGCCGCCAGACGCTGTAGCAGTTAGTGATGTAGCTCTGCTCGTGCCAGT

303 BGLI , 308 NLAIII, 324 TTH111I, 350 HGIAI SDUI, 357 HINCI

I,

361 ACTTCCGTACGGAGCCGCAGACTCCGCAGGAGTGGATCGACGACCTGGAGCGCCTCCAGG

TGAAGGCATGCCTCGGCGTCTGAGGCGTCCTCACCTAGCTGCTGGACCTCGCGGAGGTCC

357 RSAI, 380 HINFI, 394 BINI, 395 DPNI SAU3A, 404 APYI ECOR

II, 405 GSUI, 409 HAEII, 413 MNLI, 414 GSUI, 415 APYI ECORII

, 419 AVAII,

421 ACCGCTACCCCTGGCTCGTCGCCGAGGTGGAGGGCGTCGTCGCCGGCATCGCCTACGCCG

TGGCGATGGGGACCGAGCAGCGGCTCCACCTCCCGCAGCAGCGGCCGTAGCGGATGCGGC

430 APYI ECORII, 444 MNLI, 450 MNLI, 453 ACYI, 454 HGAI, 462

NAEI, 466 SFANI, 477 NAEI,

481 GCCCCTGGAAGGCCCGCAACGCCTACGACTGGACCGTCGAGTCGACGGTGTACGTCTCCC

CGGGGACCTTCCGGGCGTTGCGGATGCTGACCTGGCAGCTCAGCTGCCACATGCAGAGGG

484 APYI ECORII, 511 AVAII, 519 HINFI, 521 ACCI HIN CII SALI,

530 RSAI, 532 MAEII,

541 ACCGGCACCAGCGGCTCGGACTGGGCTCCACCCTCTACACCCACCTGCTGAAGTCC

TGGCCGTGGTCGCCGAGCCTGACCCGAGGTGGGAGATGTGGGTGGACGACTTCAGGT

544 HGICI, 549 NSPBII, 563 HGIJII SDUI, 572 MNLI, 578 TAQII,

583 BSPMI, 595 NCOI STYI, 596 NLAIII, 6000 MNLI,

601 AGGCCCAGGGCTTCAAGAGCGTGGTCGCCGTCATCGGACTGCCCAACGACCCGAGCGTGC

TCCGGGTCCCGAAGTTCTCGCACCAGCGGCAGTAGCCTGACGGGTTGCTGGGCTCGCACG

605 APYI ECORII, 650 AVAI,

661 GCCTGCACGAGGCGCTCGGATACACCGCGCGCGGGACGCTGCGGGCAGCCGGCTACAAGC

CGGACGTGCTCCGCGAGCCTATGTGGCGCGCGCCCTGCGACGCCCGTCGGCCGATGTTCG

669 MNLI, 671 HAEII, 686 FNUDII, 687 BSSHII, 688 PNUDII, 690

FNUDII, 695 HGAI, 698 BBVI, 705 BBVI, 708 NAEI, 716 TTH111I

I,

721 ACGGGGGCTGGCACGACGTGGGGTTCTGGCAGCGCGACTTCGAGCTGCCGGCCCCGCCCC

TGCCCCCGACCGTGCTGCACCCCAAGACCGTCGCGCTGAAGCTCGACGGCCGGGGCGGGG

732 DRAIII, 736 MAEII, 749 BBVI, 753 FNUDII, 763 ALUI, 764 B

BVI, 767 NAEI,

781 GCCCCGTCCGGCCCGTCACACAGATCT

CGGGGCAGGCCGGGCAGTGTGTCTAGA

795 MAEIII, 802 BGLII XHOII, 803 DPNI SAU3A,

We claim:
1. A process for the production of a PTC-resistant plant which comprises incorporating into the genome of the plant a phosphinothricin (PTC)-resistance gene obtainable by selecting *Streptomyces viridochromogenes* DSM 4112 for resistance to phosphinothricyl-alanyl-alanine (PTT), cutting with BamHI the total DNA from the resistant strains, cloning a fragment 4.0 Kb in size, and selecting for PTT resistance.

2. A process for the production of a PTC-resistant plant which comprises incorporating into the genome of the plant a phosphinothricin (PTC)-resistance gene obtainable by selecting *Streptomyces viridochromogenes* DSM 4112 for resistance to phosphinothricyl-alanyl-alanine (PTT), cutting with BamHI the total DNA from the resistant strains, cloning a fragment 4.0 Kb in size, and selecting for PTT resistance, wherein the PTC-resistance gene so-obtained has a restriction map as shown in FIG. 1.

3. A process for the production of a PTC-resistant plant which comprises incorporating into the genome of the plant a phosphinothricin (PTC)-resistance gene obtainable by selecting *Streptomyces viridochromogenes* DSM 4112 for resistance to phosphinothricyl-alanyl-alanine (PTT), cutting with BamHI the total DNA from the resistant strains, cloning a fragment 4.0 Kb in size, and selecting for PTT resistance, wherein the PTC-resistance gene so-obtained contains at least positions 258–806 of the DNA sequence I:

IleTrpSerAspValLeuGlyAlaGlyProValLeuProGlyAspAspPhePheSerLeuGlyGlyThrSerIle  75

AspLeuGluArgArgProGlyGlyArgSerGlyAlaAlaArgGlyArgLeuLeuProArgArgHisLeuHis

ArgSerGlyAlaThrSerTrpGlyProValArgCysProGlyThrThrSerSerProSerAlaAlaProPro

AGATCTGGAGCGACGTCCTGGGGGCCGGTCCGGTGCTGCCCGGGGACGACTTCTTCTCCCTCGGCGGCACCTCCA

TCTAGACCTCGCTGCAGGACCCCCGGCCAGGCCACGACGGGCCCCTGCTGAAGAAGAGGGAGCCGCCGTGGAGGT

SerArgSerArgArgGlyProProArgAspProAlaAlaArgProArgSerArgArgGlyArgArgCysArgTrp

AspProAlaValAspGlnProGlyThrArgHisGlnGlyProValValGluGluGlyGluAlaAlaGlyGlyAsp

IleGlnLeuSerThrArgProAlaProGlyThrSerGlyProSerSerLysLysGluArgProValGluMet

SerAlaLeuArgValValSerArgIleArgLysGluLeuGlyValProLeuArgLeuAlaValIlePheGluThr 150

LeuGlyValAlaGlyGlyLeuAlaHisProGlnGlyThrArgArgAlaThrProAlaArgArgAspLeuArgAsp

SerArgArgCysGlyTrpSerArgAlaSerAlaArgAsnSerAlaCysHisSerGlySerProOP SerSerArg

TCTCGGCGTTGCGGGTGGTCTCGCGCATCCGCAAGGAACTCGGCGTGCCACTCCGGCTCGCCGTGATCTTCGAGA

AGAGCCGCAACGCCCACCAGAGCGCGTAGGCGTTCCTTGAGCCGCACGGTGAGGCCGAGCGGCACTAGAAGCTCT

ArgProThrAlaProProArgAlaCysGlyCysProValArgArgAlaValGlyAlaArgArgSerArgArgSer

ArgArgGlnProHisAspArgAlaAspAlaLeuPheGluAlaHisTrpGluProGluGlyHisAspGluLeuArg

GluAlaAsnArgThrThrGluArgMetArgLeuSerSerProThrGlySerArgSerAlaThrIleLysSerVal

ProSerLeuGluAlaValAlaGluSerValLeuArgGluLeuLysGlyThrAM OC ArgGlyAlaArgHisPro 225

AlaValProGlySerGlyGlyArgIleArgThrProArgThrGluGlyAspValValLysArgCysProProPro

ArgArgProTrpLysArgTrpProAsnProTyrSerAlaAsnOP ArgGlyArgSerLysGluValProAlaThr

CGCCGTCCCTGGAAGCGGTGGCCGAATCCGTACTCCGCGAACTGAAGGGGACGTAGTAAAGAGGTGCCCGCCACC

GCGGCAGGGACCTTCGCCACCGGCTTAGGCATGAGGCGCTTGACTTCCCCTGCATCATTTCTCCACGGGCGGTGG

AlaThrGlyProLeuProProArgIleArgValGlyArgValSerProSerThrThrPheLeuHisGlyGlyGly

ArgGlyGlnPheArgHisGlyPheGlyTyrGluAlaPheGlnLeuProArgLeuLeuSerThrGlyAlaValArg

GlyAspArgSerAlaThrAlaSerAspThrSerArgSerSerPheProValTyrTyrLeuProAlaArgTrpGly

LeuSerGlnAsnThrGluGlyArgProHisValSerProGluArgArgProValGluIleArgProAlaThrAla 300

AlaPheAlaGluHisArgArgLysThrThrArgGluProArgthrThrProGlyArgAspProSerArgHisArg

ArgPheArgArgthrProLysGluAspHisThrOP AlaGlnAsnAspAlaArgSerArgSerValProProPro

CGCTTTCGCAGAACACCGAAGGAAGACCACACGTGAGCCCAGAACGACGCCCGGTCGAGATCCGTCCCGCCACCG

GCGAAAGCGTCTTGTGGCTTCCTTCTGGTGTGCACTCGGGTCTTGCTGCGGGCCAGCTCTAGGCAGGGCGGTGGC

AlaLysAlaSerCysArgLeuPheValValArgSerGlyLeuValValGlyProArgSerGlyAspArgTrpArg

LysArgLeuValGlyPheSerSerTrpValHisAlaTrpPheSerAlaArgAspLeuAspThrGlyGlyGlyGly

SerGluCysPheValSerProLeuGlycysThrLeuGlySerArgArgGlyThrSerIleArgGlyAlaValala

AlaAspMetAlaAlaValCysAspIleValAsnHisTyrIleGluThrSerThrValAsnPheArgThrGluPro 375

ArgArgHisGlyGlyGlyLeuArgHisArgGlnSerLeuHisArgAspGluHisGlyGlnLeuProTyrGlyAla

ProProThrtrpArgArgSerAlaThrSerSerIleThrThrSerArgArgAlaArgSerThrSerValArgSer

CCGCCGACATGGCGGCGGTCTGCGACATCGTCAATCACTACATCGAGACGAGCACGGTCAACTTCCGTACGGAGC

GGCGGCTGTACCGCCGCCAGACGCTGTAGCAGTTAGTGATGTAGCTCTGCTCGTGCCAGTTGAAGGCATGCCTCG

ArgArgCysProProProArgArgCysArgOP AspSerCysArgSerSerCysProOP SerGlyTyrProAla

GlyValHisArgArgAspAlaValAspAspIleValValAspLeuArgAlaArgAspValGluThrArgLeuArg

AlaSerMetAlaAlaThrGlnSerMetThrLeuOP AM Met SerValLeuValThrLeuLysArgValSerGly

GlnThrProGlnGluTrpIleAspaspLeuGluArgLeuGlnAspArgTyrProTrpLeuValAlaGluValGlu 450

AlaAspSerAlaGlyValAspArgArgProGlyAlaProProGlyProLeuProLeuAlaArgArgArgGlyGly

ArgArgLeuArgArgSerGlySerThrThrTrpSerAlaSerArgThrAlaThrProGlySerSerProArgTrp

CGCAGACTCCGCAGGAGTGGATCGACGACCTGGAGCGCCTCCAGGACCGCTACCCCTGGCTCGTCGCCGAGGTGG

GCGTCTGAGGCGTCCTCACCTAGCTGCTGGACCTCGCGGAGGTCCTGGCGATGGGGACCGAGCAGCGGCTCCACC

AlaSerGluAlaProThrSerArgArgGlyProAlaGlyGlyProGlySerGlyArgAlaArgArgProPro

LeuSerArgLeuLeuProAspValValGlnLeuAlaGluLeuValAlaValGlyProGluAspGlyLeuHisLeu

-continued

CysValGlyCysSerHisIleSerSerArgSerArgArgTrpSerArgAM GlyGlnSerThrAlaSerThrSer

GlyValValAlaGlyIleAlaTyrAlaGlyProTrpLysAlaArgAsnAlaTyrAspTrpThrValGluSerThr 525

GlyArgArgArgArgHisArgLeuArgArgProLeuGluGlyProGlnArgLeuArgLeuAspArgArgValAsp

ArgAlaSerSerProAlaSerProThrProAlaProGlyArgProAlaThrProThrThrGlyProSerSerArg

AGGGCGTCGTCGCCGGCATCGCCTACGCCGGCCCCTGGAAGGCCCGCAACGCCTACGACTGGACCGTCGAGTCGA

TCCCGCAGCAGCGGCCGTAGCGGATGCGGCCGGGGACCTTCCGGGCGTTGCGGATGCTGACCTGGCAGCTCAGCT

ProArgArgArgArgCysArgArgArgArgGlyArgSerProGlyCysArgArgArgSerSerArgArgThrSer

AlaAspAspGlyAlaAspGlyValGlyAlaGlyProLeuGlyAlaValGlyValValProGlyAspLeuArgArg

ProThrThrAlaProMetAlaAM AlaProGlyGlnPheAlaArgLeuAlaAM SerGlnValThrSerAspVal

ValTyrValSerHisArgHisGlnArgLeuGlyLeuGlySerThrLeuTyrThrHisLeuLeuLysSerMetGlu 600

GlyValArgLeuProProAlaProAlaAlaArgThrGlyLeuHisProLeuHisProProAlaGluValHisGly

ArgCysThrSerProThrGlyThrSerGlySerAspTrpAlaProProSerThrProThrCysOP SerProTrp

CGGTGTACGTCTCCCACCGGCACCAGCGGCTCGGACTGGGCTCCACCCTCTACACCCACCTGCTGAAGTCCATGG

GCCACATGCAGAGGGTGGCCGTGGTCGCCGAGCCTGACCCGAGGTGGGAGATGTGGGTGGACGACTTCAGGTACC

ProThrArgArgGlyGlyAlaGlyAlaAlaArgValProSerTrpGlyArgCysGlyGlyAlaSerThrTrpPro

HisValAspGlyValProValLeuProGluSerGlnAlaGlyGlyGluValGlyValGlnGlnLeuGlyHisLeu

ThrTyrThrGluTrpArgCysTrpArgSerProSerProGluValArgAM ValTrpArgSerPheAspMetSer

AlaGlnGlyPheLysSerValValAlaValIleGlyLeuProAsnAspProSerValArgLeuHisGluAlaLeu 675

GlyProGlyLeuGlnGluArgGlyArgArgHisArgThrAlaGlnArgProGluArgAlaProAlaArpGlyAla

ArgProArgAlaSerArgAlaTrpSerProSerSerAspCysProThrThrArgAlaCysAlaCysThrAegArg

AGGCCCAGGGCTTCAAGAGCGTGGTCGCCGTCATCGGACTGCCCAACGACCCGAGCGTGCGCCTGCACGAGGCGC

TCCGGGTCCCGAAGTTCTCGCACCAGCGGCAGTAGCCTGACGGGTTGCTGGGCTCGCACGCGGACGTGCTCCGCG

ProGlyProSerOP SerArgProArgArgOP ArgValAlaTrpArgGlySerArgAlaGlyAlaArgProAla

GlyLeuAlaGluLeuAlaHisAspGlyAspAspSerGlnGlyValValArgAlaHisAlaGlnValLeuArgGlu

AlaTrpProLysLeuLeuThrThrAlaThrMetProSerGlyLeuSerGlyLeuThrArgArgCysSerAlaSer

GlyTyrThrAlaArgGlyThrLeuArgAlaAlaGlyTyrLysHisGlyGlyTrpHisAspValGlyPheTrpGln 750

ArgIleHisArgAlaArgAspAlaAlaGlySerArgLeuGlnAlaArgGlyLeuAlaArgArgGlyValLeuAla

SerAspThrProArgAlaGlyArgCysGlyGlnProAlaThrSerThrGlyAlaGlyThrThrTrpGlySerGly

TCGGATACACCGCGCGCGGGACGCTGCGGGCAGCCGGCTACAAGCACGGGGGCTGGCACGACGTGGGGTTCTGGC

AGCCTATGTGGCGCGCGCCCTGCGACGCCCGTCGGCCGATGTTCGTGCCCCCGACCGTGCTGCACCCCAAGACCG

ArgIleCysArgAlaArgSerAlaAlaProLeuArgSerCysAlaArgProSerAlaArgArgProThrArgAla

SerValGlyArgAlaProArgGlnProCysGlyAlaValLeuValProAlaProValValHisProGluProLeu

ProTyrValAlaArgProValSerArgAlaAlaProAM LeuCysProProGlnCysSerThrProAsnGlnCys

ArgAspPheGluLeuProAlaProProArgProValArgProValThrGlnIle 807

AlaArgLeuArgAlaAlaGlyProAlaProProArgProAlaArgHisThrAsp

SerAlaThrSerSerCysArgProArgProAlaProSerGlyProSerHisArgSer

AGCGCGACTTCGAGCTGCCGGCCCCGCCCCGCCCCGTCCGGCCCGTCACACAGATCT

TCGCGCTGAAGCTCGACGGCCGGGGCGGGGCGGGGCAGGCCGGGCAGTGTGTCTAGA

AlaArgSerArgAlaAlaProGlyAlaGlyGlyArgGlyAlaArgOP ValSerArg

AlaValGluLeuGlnArgGlyArgGlyAlaGlyAspProGlyAspCysLeuAsp

ArgSerLysSerSerGlyAlaGlyGlyArgGlyThrArgGlyThrValCysIle.

-continued

4. A plant which contains the PTC-resistance gene said gene is obtainable by selecting *Streptomyces viridochromogenes* DSM 4112 for resistance to phosphinothricyl-alanyl-alanine (PTT), cutting with BamHI the total DNA from the resistant strains, cloning a fragment 4.0 Kb in size, and selecting for PTC resistance.

5. A plant which contains the PTC-resistance gene said gene is obtainable by selecting *Streptomyces viridochromogenes* DSM 4112 for resistance to phosphinothricyl-alanyl-alanine (PTT), cutting with BamHI the total DNA from the resistant strains, cloning a fragment 4.0 Kb in size, and selecting for PTT resistance, wherein the PTC-resistance gene so obtained has a restriction map as shown in FIG. 1.

6. A plant which contains the PTC-resistance gene said gene obtainable by selecting *Streptomyces viridochromogenes* DSM 4112 for resistance to phosphinothricyl-alanyl-alanine (PTT), cutting with BamHI the total DNA from the resistant strains, cloning a fragment 4.0 Kb in size, and selecting for PTT resistance, wherein the PTC-resistance gene so obtained contains at least positions 258–806 of the DNA sequence I:

IleTrpSerAspValLeuGlyAlaGlyProValLeuProGlyAspAspPhePheSerLeuGlyGlyThrSerIle

AspLeuGluArgArgProGlyGlyArgSerGlyAlaAlaArgGlyArgLeuLeuLeuProArgArgHisLeuHis

ArgSerGlyAlaThrSerTrpGlyProValArgCysCysProGlyThrThrSerSerProSerAlaAlaProPro

AGATCTGGAGCGACGTCCTGGGGGCCGGTCCGGTGCTGCCCGGGGACGACTTCTTCTCCCTCGGCGGCACCTCCA 75

TCTAGACCTCGCTGCAGGACCCCCGGCCAGGCCACGACGGGCCCCTGCTGAAGAAGAGGGAGCCGCCGTGGAGGT

SerArgSerArgArgGlyProProArgAspProAlaAlaArgProArgSerArgArgGlyArgArgCysArgTrp

AspProAlaValAspGlnProGlyThrArgHisGlnGlyProValValGluGluGlyGluAlaAlaGlyGlyAsp

IleGlnLeuSerThrArgProAlaProGlyThrSerGlyProSerSerLysLysGluArgProProValGluMet

SerAlaLeuArgValValSerArgIleArgLysGluLeuGlyValProLeuArgLeuAlaValIlePheGluThr

LeuGlyValAlaGlyGlyLeuAlaHisProGlnGlyThrArgArgAlaThrProAlaArgArgAspLeuArgAsp

SerArgArgCysGlyTrpSerArgAlaSerAlaArgAsnSerAlaCysHisSerGlySerProOP SerSerArg

TCTCGGCGTTGCGGGTGGTCTCGCGCATCCGCAAGGAACTCGGCGTGCCACTCCGGCTCGCCGTGATCTTCGAGA 150

AGAGCCGCAACGCCCACCAGAGCGCGTAGGCGTTCCTTGAGCCGCACGGTGAGGCCGAGCGGCACTAGAAGCTCT

ArgProThrAlaProProArgAlaCysGlyCysProValArgArgAlaValGlyAlaArgArgSerArgArgSer

ArgArgGlnProHisAspArgAlaAspAlaLeuPheGluAlaHisTrpGluProGluGlyHisAspGluLeuArg

GluAlaAsnArgThrThrGluArgMetArgLeuSerSerProThrGlySerArgSerAlaThrIleLysSerVal

ProSerLeuGluAlaValAlaGluSerValLeuArgGluLeuLysGlyThrAM OC ArgGlyAlaArgHisPro

AlaValProGlySerGlyGlyArgIleArgThrProArgThrGluGlyAspValValLysArgCysProProPro

ArgArgProTrpLysArgTrpProAsnProTyrSerAlaAsnOP ArgGlyArgSerLysGluValProAlaThr

CGCCGTCCCTGGAAGCGGTGGCCGAATCCGTACTCCGCGAACTGAAGGGGACGTAGTAAAGAGGTGCCCGCCACC 225

GCGGCAGGGACCTTCGCCACCGGCTTAGGCATGAGGCGCTTGACTTCCCCTGCATCATTTCTCCACGGGCGGTGG

AlaThrGlyProLeuProProArgIleArgValGlyArgValSerProSerThrThrPheLeuHisGlyGlyGly

ArgGlyGlnPheArgHisGlyPheGlyTyrGluAlaPheGlnLeuProArgLeuLeuSerThrGlyAlaValArg

GlyAspArgSerAlaThrAlaSerAspThrSerArgSerSerPheProValTyrTyrLeuProAlaArgTrpGly

LeuSerGlnAsnThrGluGlyArgProHisValSerProGluArgArgProValGluIleArgProAlaThrAla

AlaPheAlaGluHisArgArgLysThrThrArgGluProArgThrThrProGlyArgAspProSerArgHisArg

ArgPheArgArgThrProLysGluAspHisThrOP AlaGlnAsnAspAlaArgSerArgSerValProProPro

CGCTTTCGCAGAACACCGA<u>AGGAAG</u>ACCACAC<u>GTG</u>AGCCCAGAACGACGCCCGGTCGAGATCCGTCCCGCCACCG 300

GCGAAAGCGTCTTGTGGCTTCCTTCTGGTGTGCACTCGGGTCTTGCTGCGGGCCAGCTCTAGGCAGGGCGGTGGC

AlaLysAlaSerCysArgLeuPheValValArgSerGlyLeuValValGlyProArgSerGlyAspArgTrpArg

LysArgLeuValGlyPheSerSerTrpValHisAlaTrpPheSerAlaArgAspLeuAspThrGlyGlyGylGly

SerGluCysPheValSerProLeuGlyCysThrLeuGlySerArgArgGlyThrSerIleArgGlyAlaValAla

AlaAspMetAlaAlaValCysAspIleValAsnHisTyrIleGluThrSerThrValAsnPheArgThrGluPro

ArgArgHisGlyGlyGlyLeuArgHisArgGlnSerLeuHisArgAspGluHisGlyGlnLeuProTyrGlyAla

ProProThrTrpArgArgSerAlaThrSerSerIleThrThrSerArgArgAlaArgSerThrSerValArgSer

CCGCCGACATGGCGGCGGTCTGCGACATCGTCAATCACTACATCGAGACGAGCACGGTCAACTTCCGTACGGAGC 375

GGCGGCTGTACCGCCGCCAGACGCTGTAGCAGTTAGTGATGTAGCTCTGCTCGTGCCAGTTGAAGGCATGCCTCG

ArgArgCysProProProArgArgCysArgOP AspSerCysArgSerSerCysProOP SerGlyTyrProAla

GlyValHisArgArgAspAlaValAspAspIleValValAspLeuArgAlaArgAspValGluThrArgLeuArg

AlaSerMetAlaAlaThrGlnSerMetThrLeuOP AM MetSerValLeuValThrLeuLysArgValSerGly

GlnThrProGlnGluTrpIleAspAspLeuGluArgLeuGlnAspArgTyrProTrpLeuValAlaGluValGlu

AlaAspSerAlaGlyValAspArgArgProGlyAlaProProGlyProLeuProLeuAlaArgArgArgGlyGly

ArgArgLeuArgSerGlySerThrThrTrpSerAlaSerArgThrAlaThrProGlySerSerProArgTrp

CGCAGACTCCGCAGGAGTGGATCGACGACCTGGAGCGCCTCCAGGACCGCTACCCCTGGCTCGTCGCCGAGGTGG 450

GCGTCTGAGGCGTCCTCACCTAGCTGCTGGACCTCGCGGAGGTCCTGGCGATGGGGACCGAGCAGCGGCTCCACC

AlaSerGluAlaProThrSerArgArgGlyProAlaGlyGlyProGlySerGlyArgAlaArgArgArgProPro

LeuSerArgLeuLeuProAspValValGlnLeuAlaGluLeuValAlaValGlyProGluAspGlyLeuHisLeu

CysValGlyCysSerHisIleSerSerArgSerArgArgTrpSerArgAM GlyGlnSerThrAlaSerThrSer

GlyValValAlaGlyIleAlaTyrAlaGlyProTrpLysAlaArgAsnAlaTyrAspTrpThrValGluSerThr

GlyArgArgArgArgHisArgLeuArgArgProLeuGluGlyProGlnArgLeuArgLeuAspArgArgValAsp

ArgAlaSerSerProAlaSerProThrProAlaProGlyArgProAlaThrProThrThrGlyProSerSerArg

AGGGCGTCGTCGCCGGCATCGCCTACGCCGGCCCCTGGAAGGCCCGCAACGCCTACGACTGGACCGTCGAGTCGA 525

TCCCGCAGCAGCGGCCGTAGCGGATGCGGCCGGGGACCTTCCGGGCGTTGCGGATGCTGACCTGGCAGCTCAGCT

ProArgArgArgArgCysArgArgArgArgGlyArgSerProGlyCysArgArgArgSerSerArgArgThrSer

AlaAspAspGlyAlaAspGlyValGlyAlaGlyProLeuGlyAlaValGlyValValProGlyAspLeuArgArg

ProThrThrAlaProMetAlaAM AlaProGlyGlnPheAlaArgLeuAlaAM SerGlnValThrSerAspVal

ValTyrValSerHisArgHisGlnArgLeuGlyLeuGlySerThrLeuTyrThrHisLeuLeuLysSerMetGlu

GlyValArgLeuProProAlaProAlaAlaArgThrGlyLeuHisProLeuHisProProAlaGluValHisGly

ArgCysThrSerProThrGlyThrSerGlySerAspTrpAlaProProSerThrProThrCysOP SerProTrp

CGGTGTACGTCTCCCACCGGCACCAGCGGCTCGGACTGGGCTCCACCCTCTACACCCACCTGCTGAAGTCCATGG 600

GCCACATGCAGAGGGTGGCCGTGGTCGCCGAGCCTGACCCGAGGTGGGAGATGTGGGTGGACGACTTCAGGTACC

ProThrArgArgGlyGlyAlaGlyAlaAlaArgValProSerTrpGlyArgCysGlyGlyAlaSerThrTrpPro

HisValAspGlyValProValLeuProGluSerGlnAlaGlyGlyGluValGlyValGlnGlnLeuGlyHisLeu

ThrTyrThrGluTrpArgCysTrpArgSerProSerProGluValArgAM ValTrpArgSerPheAspMetSer

AlaGlnGlyPheLysSerValValAlaValIleGlyLeuProAsnAspProSerValArgLeuHisGluAlaLeu

GlyProGlyLeuGlnGluArgGlyArgArgHisArgThrAlaGlnArgProGluArgAlaProAlaArgGlyAla

ArgProArgAlaSerArgAlaTrpSerProSerSerAspCysProThrThrArgAlaCysAlaCysThrArgArg

AGGCCCAGGGCTTCAAGAGCGTGGTCGCCGTCATCGGACTGCCCAACGACCCGAGCGTGCGCCTGCACGAGGCGC 675

TCCGGGTCCCGAAGTTCTCGCACCAGCGGCAGTAGCCTGACGGGTTGCTGGGCTCGCACGCGGACGTGCTCCGCG

ProGlyProSerOP SerArgProArgArgOP ArgValAlaTrpArgGlySerArgAlaGlyAlaArgProAla

-continued

GlyLeuAlaGluLeuAlaHisAspGlyAspAspSerGlnGlyValValArgAlaHisAlaGlnValLeuArgGlu

AlaTrpProLysLeuLeuThrThrAlaThrMetProSerGlyLeuSerGlyLeuThrArgArgCysSerAlaSer

GlyTyrThrAlaArgGlyThrLeuArgAlaAlaGlyTyrLysHisGlyGlyTrpHisAspValGlyPheTrpGln

ArgIleHisArgAlaArgAspAlaAlaGlySerArgLeuGlnAlaArgGlyLeuAlaArgArgGlyValLeuAla

SerAspThrProArgAlaGlyArgCysGlyGlnProAlaThrSerThrGlyAlaGlyThrThrTrpGlySerGly

TCGGATACACCGCGCGCGGGACGCTGCGGGCAGCCGGCTACAAGCACGGGGGCTGGCACGACGTGGGGTTCTGGC 750

AGCCTATGTGGCGCGCGCCCTGCGACGCCCGTCGGCCGATGTTCGTGCCCCCGACCGTGCTGCACCCCAAGACCG

ArgIleCysArgAlaArgSerAlaAlaProLeuArgSerCysAlaArgProSerAlaArgArgProThrArgAla

SerValGlyArgAlaProArgGlnProCysGlyAlaValLeuValProAlaProValValHisProGluProLeu

ProTyrValAlaArgProValSerArgAlaAlaProAM LeuCysProProGlnCysSerThrProAsnGlnCys

ArgAspPheGluLeuProAlaProProArgProValArgProValThrGlnIle

AlaArgLeuArgAlaAlaGlyProAlaProProArgProAlaArgHisThrAsp

SerAlaThrSerSerCysArgProArgProAlaProSerGlyProSerHisArgSer

AGCGCGACTTCGAGCTGCCGGCCCCGCCCCGCCCCGTCCGGCCCGTCACACAGATCT 807

TCGCGCTGAAGCTCGACGGCCGGGGCGGGGCGGGGCAGGCCGGGCAGTGTGTCTAGA

AlaArgSerArgAlaAlaProGlyAlaGlyGlyArgGlyAlaArgOP ValSerArg

AlaValGluLeuGlnArgGlyArgGlyAlaGlyAspProGlyAspCysLeuAsp

ArgSerLysSerSerGlyAlaGlyGlyArgGlyThrArgGlyThrValCysIle.

\* \* \* \* \*

UNITED STATES PATENT AND TRADEMARK OFFICE
CERTIFICATE OF CORRECTION

PATENT NO.   : 5,637,489
DATED        : June 10, 1997
INVENTOR(S)  : Eckhard STRAUCH et al.

It is certified that error appears in the above-identified patent and that said Letters Patent is hereby corrected as shown below:

```
Claim 3, columns 11 - 12, in sequence listing,
    line 3, after "Cys", insert --Cys--.

Claim 3, columns 13 - 14, in sequence listing,
    line 20, "thr" should read --Thr--;
    line 21, "thr" should read --Thr--;
    line 26, "cys" should read --Cys--,
         and "ala" should read --Ala--;
    line 29, "trp" should read --Trp--; and
    line 35, "asp" should read --Asp--.

Claim 3, columns 15 - 16, in sequence listing,
    line 19, "Arp" should read --Arg--; and
    line 20, "Aeg" should read --Arg--.
```

Signed and Sealed this

Twenty-eighth Day of April, 1998

Attest:

BRUCE LEHMAN

*Attesting Officer*   Commissioner of Patents and Trademarks